United States Patent [19]

Fenyes et al.

[11] 4,181,806

[45] Jan. 1, 1980

[54] AMINOALKYLENEPHOSPHONIC ACIDS AND SALTS THEREOF AND THEIR USE IN AQUEOUS SYSTEMS

[75] Inventors: Joseph G. E. Fenyes, Germantown; John D. Pera, Memphis, both of Tenn.

[73] Assignee: Buckman Laboratories, Inc., Memphis, Tenn.

[21] Appl. No.: 914,250

[22] Filed: Jun. 9, 1978

[51] Int. Cl.$^2$ .......................................... C07D 333/48
[52] U.S. Cl. .......................................... 549/6; 549/68; 260/944; 252/389 A; 422/15
[58] Field of Search ........ 260/329 P, 329 AM, 332.1, 260/944; 252/389 A; 422/15; 71/67

[56] References Cited

U.S. PATENT DOCUMENTS

| | | | |
|---|---|---|---|
| 3,546,216 | 12/1970 | Dunn | 260/332.1 |
| 3,705,005 | 12/1972 | Cervi et al. | 422/15 |
| 4,101,441 | 7/1978 | Hwa et al. | 252/389 A |
| 4,120,686 | 10/1978 | Paulus et al. | 71/67 |

Primary Examiner—Bernard Helfin
Assistant Examiner—L. Hendriksen
Attorney, Agent, or Firm—Floyd Trimble

[57] ABSTRACT

Aminoalkylenephosphonic acids and their alkali metal salts prepared by a reaction utilizing a primary or secondary tetrahydrothiophenamine 1,1-dioxide or the hydrochloride thereof, an aldehyde or a ketone, and orthophosphorous acid are useful in the control of scale and sludge deposition in aqueous systems. When used in combination with known corrosion inhibitors they show synergistic results in inhibiting corrosion of metal surfaces in contact with an aqueous system that is normally corrosive to such metals.

17 Claims, No Drawings

AMINOALKYLENEPHOSPHONIC ACIDS AND SALTS THEREOF AND THEIR USE IN AQUEOUS SYSTEMS

This invention relates to phosphonalkylene derivatives of tetrahydrothiophenamine 1,1-dioxides and the use of the same for inhibiting the deposition of scale and sludge on heat transfer surfaces of cooling water systems and boilers. The new compositions of matter useful in our invention may be also defined as aminoalkylenephosphonic acids and their alkali metal salts having the formula:

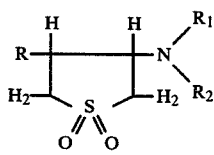

wherein R is hydrogen or

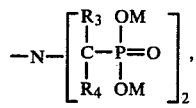

$R_1$ is hydrogen or

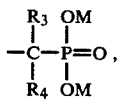

$R_2$ is an alkyl group containing 1 to 4 carbon atoms, 2-hydroxyethyl, 2-hydroxypropyl, 3-chloro-2-hydroxypropyl,

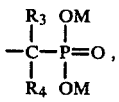

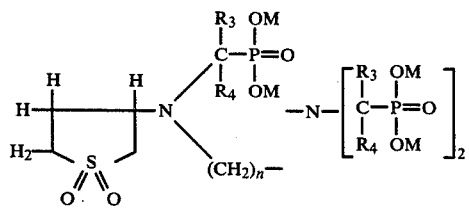

$R_3$ and $R_4$ may be the same or different and are selected from the group consisting of hydrgen and an alkyl containing 1 to 4 carbon atoms; n is 1 or 2; M is hydrogen or an alkali metal; with the proviso that when R is

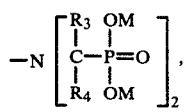

$R_2$ is

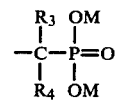

and with the further proviso in that $R_1$ is hydrogen only when $R_2$ is

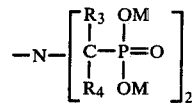

The phosphonalkylene tetrahydrothiophenamine 1,1-dioxides are prepared by conventional methods utilizing primary or secondary tetrahydrothiophenamine 1,1-dioxides or their hydrochlorides, an aldehyde or a ketone, and orthophosphorous acid.

The primary and secondary tetrahydrothiophenamine 1,1-dioxides used in the preparation of the compositions of this invention are prepared usually by the reaction of 2,5-dihydrothiophene 1,1-dioxide with ammonia and primary amines. Typical examples of amines that can be used are tetrahydro-3-thiophenamine 1,1-dioxide, tetrahydro-N-methyl-3-thiophenamine 1,1-dioxide, N-ethyltetrahydro-3-thiophenamine 1,1-dioxide, tetrahydro-N-propyl-3-thiophenamine 1,1-dioxide, N-n-butyltetrahydro-3-thiophenamine 1,1-dioxide, tetrahydro-N-isopropyl-3-thiophenamine 1,1-dioxide, tetrahydro-N-isobutyl-3-thiophenamine 1,1-dioxide, N-sec-butyltetrahydro-3-thiophenamine 1,1-dioxide, tetrahydro-N-(2-hydroxyethyl)-3-thiophenamine 1,1-dioxide, tetrahydro-N-(2-hydroxypropyl)-3-thiophenamine 1,1-dioxide, N-(3-chloro-2-hydroxypropyl) tetrahydro-3-thiophenamine 1,1-dioxide, tetrahydro-3,4-thiophendiamine 1,1-dioxide, N,N'-methylenebis(tetrahydro-3-thiophenamine)1,1,1',1'-tetraoxide, and N,N'-ethylenebis(tetrahydro-3-thiophenamine)1,1,1',1'-tetraoxide.

Aldehydes and ketones that can be used in the processes of this invention have the formula:

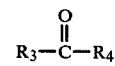

wherein $R_3$ and $R_4$ are the same or different and are selected from the group consisting of hydrogen and alkyl groups containing 1 to 4 carbon atoms.

Typical examples of suitable aldehydes are formaldehyde, acetaldehyde, propionaldehyde, and butyraldehyde. Typical examples of suitable ketones are acetone, methylethylketone, 2-pentanone, methyl isobutyl ketone, and diethylketone.

Orthophosphorous acid is readily available commercially. It can be utilized in the processes of the present invention either as the acid, or in the form of its salts, such as its mono- or di-alkali metal salts. When orthophosphorous acid is utilized in the salt form, usually a small amount of a supplementary acid should also be utilized in order to effectively convert the salt form into the more reactive orthophosphorous acid.

Cooling water systems are subject to formation of scale deposits. Scaling can occur when the concentration of a dissolved substance in a cooling water becomes greater than its solubility in the water. It can especially be a problem with a substance that has an inverse solubility curve, that is, a material whose solubility goes down as the temperature goes up. Since water temperatures at or near heat-transfer surfaces are greater than temperatures in the bulk of the system, the solubility of such materials is less in these regions. Consequently, they tend to precipitate and form scales that reduce heat-transfer efficiency.

One principal scale-forming material encountered in cooling water systems is calcium carbonate formed by the decomposition of calcium bicarbonate. This compound not only has an inverse solubility curve, but its solubility is much lower in most typical cooling waters than almost all other potential scale-formers that might be present in these waters. Of course, calcium carbonate is soluble in acidic solutions, and as the pH of a cooling water is lowered, scale generally becomes less of a problem. However, most cooling waters are kept on the alkaline side to reduce corrosion, and thus calcium carbonate scaling remains as a potential problem. Calcium sulfate, calcium phosphate, barium sulfate, and ferric hydroxide can also cause scale. Thus, to be a broadly useful composition, a scale control product must be capable of controlling different scale types.

It is well known that the operation of commercial and industrial cooling systems is adversely affected by a number of different factors. Of these adverse factors, corrosion of metallic parts coming into contact with the water is probably one of the most serious. If not controlled, corrosion causes the rapid deterioration of the metallic materials of construction used in cooling towers and associated equipment such as pumps, pipelines and valves, causing major losses in overall efficiency of the cooling systems. While control of bleedoff, pH, and other operating variables is helpful in reducing corrosion, chemical treatment of the water is generally the most effective and economical means of minimizing this problem, particularly where conservation of water by means of recycling is necessary or desired.

Waterside problems encountered in boilers and steam systems include the formation of scale and other deposits, corrosion, and foam. Scale and other deposits on heat-transfer surfaces can cause loss of the thermal efficiency of the boiler and can make the temperature of the boiler metal increase. Under scaling conditions, temperatures may go high enough to lead to failure of the metal due to overheating. Corrosion in boilers and steam systems also cause failure of boiler metal and damage to steam and condensate lines.

The principal source of deposits in boilers is dissolved mineral matter in the boiler feedwater. The term, "scale", is generally used for deposits that adhere to boiler surfaces exposed to the water, while nonadherent deposits are called, "sludge" or "mud". Scale causes more difficulty because the sludge can be purged from the system with the blowdown or can be easily washed out, but scale can normally only be removed by mechanical or chemical cleaning of the boiler.

In natural, untreated water the main sources of scale and sludge are calcium carbonate, calcium sulfate, magnesium hydroxide, and silica. The most common type of scale in boilers is probably calcium carbonate, but the most troublesome is usually calcium sulfate. The latter causes more difficulties because its solubility decreases more rapidly with increasing temperatures than does that of other substances, and the scale it forms is hard, dense, and difficult to remove. On the other hand, calcium carbonate tends to form sludge more than scale, and the calcium carbonate scales that do form are generally softer and easier to remove. Magnesium hydroxide precipitates are not very adherent and tend to form sludges rather than scales.

The aminoalkylenephosphonic acids and salts of our invention may be utilized as solids, as solutions in water or in polar organic solvents or in combinations of water and solvents. When used for scale inhibition the aminoalkylenephosphonates may be used alone or in combination with other scale inhibitors. Examples of these would be alkali metal phosphates, alkali metal polyphosphates, alkali metal tripolyphosphates, alkali metal pyrophosphates, organic water soluble polymers containing a linear hydrocarbon structure with side chain carboxylic acid groups exemplified by the structure:

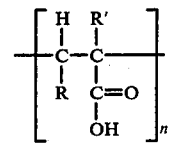

where R is hydrogen or —COOH and R' is hydrogen or methyl. These polymers may be obtained from acrylic acid or methacrylic acid. Polymers of maleic anhydride can be prepared and the anhydride group hydrolyzed with water to provide carboxylic acid groups. Acrylonitrile and acrylamide polymers may also be hydrolyzed with hot alkaline solutions to eliminate ammonia and form carboxylic acid salts. Copolymers of all of the monomers listed may also be prepared and these copolymers may be hydrolyzed to the carboxylic acid groups if the anhydride, amide, or nitrile groups are contained in the copolymers. These polymers may be utilized as the free acid or as water soluble salts such as the alkali metal and alkaline earth metal salts. The polymers used in this invention are either commercially available or methods for their preparation are well known in the art. In addition, poly(acrylamide) of low molecular weight may be combined with the phosphonates of this invention.

The aminoalkylenephosphonic acids of this invention can be formulated with such polymers as poly(acrylic acid) with both ingredients used as the free acids. This is advantageous when the products are used in closed systems such as recirculated cooling water systems. In such systems, the evaporation of water increases the solids content of the water and increases the pH at the same time, particularly if alkaline scale inhibitors are being added. The cycles of concentration in those systems can be markedly increased if the additive has an acid pH.

The aminoalkylenephosphonates of this invention act as corrosion inhibitors for mild steel if relatively high concentrations are used. Formulations of these phosphonates with corrosion inhibitors such as water soluble zinc salts will provide both scale inhibition and synergistic corrosion protection. Combinations of the phosphonates with 2-mercaptobenzothiazole, benzotriazole, and tolyltriazole will give good corrosion inhibition on both copper alloys and steel. Additional compounds which have been used as corrosion inhibitors and which can be used in combination with the aminoalkylenephosphonates of this invention include phosphates, polyphosphates, organic water-soluble polymers, silicates, dithiocarbamates, nitrites, oxazoles, imidazoles, lignins, lignosulfonate, tannins, phosphoric acid esters, boric acid esters, alkali metal salts of inorganic molybdenum and chromium compounds.

It is an object of the present invention to provide novel aminoalkylenephosphonic acids having valuable properties.

It is another object of this invention to provide the alkali metal salts of such novel aminoalkylenephosphonic acids.

A further object of the present invention is to provide a composition that is compatible with other water treatment agents to achieve maximum efficiency in the control of both scale and corrosion.

These and other objects and advantages will become apparent as the description proceeds.

To the accomplishment of the foregoing and related ends, this invention then comprises the features hereinafter fully described and particularly pointed out in the claims, the following description setting forth in detail certain illustrative embodiments of the invention, these being indicative, however, of but a few of the various ways in which the principles of the invention may be employed.

The amount and manner of use of the scale, sludge, and corrosion control compositions of our invention are dependent on the nature of the problems caused by scale and sludge in the particular system. In general, suitable quantities of the aminoalkylenephosphonic acid or its salt vary from 0.5 to 500 parts per million parts by weight of water. Preferred quantities vary from 1.0 to 200 parts per million parts of water. It is understood, of course, that larger quantities may be used, but such is generally not desirable because costs are increased without commensurate additional beneficial results.

In order to disclose the nature of the invention still more clearly, the following illustrative examples will be given. It is understood, however, that the invention is not to be limited to the specific conditions or details set forth in these examples, except insofar as such limitations are specified in the appended claims.

EXAMPLE 1

Tetrahydro-3-thiophenamine 1,1-dioxide hydrochloride

A solution of 2,5-dihydrothiophene 1,1-dioxide (50.0 parts) in 29 percent $NH_4OH$ (180 ml.) was heated in a 1 liter stainless steel autoclave at 80°–86° C. for 7 hours. The mixture was concentrated under reduced pressure to a yellow oil which was filtered, dissolved in ethanol (150 ml.) and treated with concentrated HCl (100 ml.) Addition of ethyl ether (100 ml.) to the resultant mixture precipitated the crystalline hydrochloride, which was collected, washed with ether and dried in vacuo over $P_2O_5$. m.p. 220° C. Yield 54.9 g. (75.5 percent of the theory).

EXAMPLE 2

N-Methyltetrahydro-3-thiophenamine 1,1-dioxide hydrochloride

The procedure of Example 1 was repeated substituting 50 percent aqueous monomethylamine (174 ml.) for the ammonium hydroxide of Example 1. Sixty-four and seven-tenths grams of a white crystalline solid was obtained for a yield of 82.2 percent of theory based upon the 2,5-dihydrothiophene 1,1-dioxide. The solid sublimes over 180° C. and metls between 205° and 210° C.

EXAMPLE 3

N-Hydroxyethyltetrahydro-3-thiophenamine 1,1-dioxide hydrochloride

The procedure of Example 1 was repeated substituting 95 percent monoethanolamine (28.6 parts) for the ammonium hydroxide of Example 1. A sticky solid was filtered after treatment with hydrochloric acid, and upon drying in vacuo over $P_2O_5$ weighed 59.6 g. (78.5 percent of theory) m.p. 122°–124° C.

EXAMPLE 4

Tetrahydro-N,N-bis(phosphonomethyl)-3-thiophenamine 1,1-dioxide

Method 1:

A mixture of tetrahydro-3-thiophenamine 1,1-dioxide hydrochloride (171.6 parts, 1.0 mole); 258 parts of 70 percent aqueous orthophosphorous acid (2.2 moles); and 73.4 parts of 90 percent paraformaldehyde (2.2 moles) was refluxed for 3 hours. After cooling the mixture was stirred into 750 ml. of ethanol. The white, sticky precipitate obtained was triturated under ethanol to give a filterable white hygroscopic solid that upon drying over $P_2O_5$ in a vacuum dessicator weighed 163.7 g. (50.6 percent of the theory).

Method 2:

To tetrahydro-3-thiophenamine 1,1-dioxide (270.4 parts, 2.0 moles); and concentrated hydrochloric acid (197.2 parts, 2.0 moles) was added at such a rate as to keep the temperature below 50° C. This was followed by the addition of 70 percent aqueous orthophosphorous acid (468.6 parts, 4.0 moles). The resulting mixture was heated to 60°–65° C. at which temperature 37 percent aqueous formaldehyde (356.8 parts, 4.4 moles) was introduced during a period of 30–40 minutes. Heating was continued and the temperature rose to 180° C. and the mixture was refluxed for 1 hour after the addition of formaldehyde was completed. A 50 percent aqueous solution of the title compound was obtained.

EXAMPLE 5

Tetrahydro-N-methyl-N-(phosphonomethyl)-3-thiophenamine 1,1-dioxide

A mixture of N-methyltetrahydro-3-thiophenamine 1,1-dioxide hydrochloride (37.2 parts, 0.20 mole); 90 percent paraformaldehyde (6.8 parts, 0.22 mole); orthophosphorous acid (18.0 parts, 0.22 mole); and water (30 parts) was heated at its reflex temperature for 3 hours. After cooling, the solution was stirred into ethanol (150 ml.) and the sticky, white precipitate was triturated under more ethanol. After being dried in vacuo over $P_2O_5$ the product weighed 42.0 g. (86.3 percent yield). m.p. 222°–225° C.

EXAMPLE 6

Tetrahydro-N-(2-hydroxyethyl)-N-(phosphonomethyl)-3-thiophenamine 1,1-dioxide

A solution of tetrahydro-N-hydroxymethyl-3-thiophenamine 1,1-dioxide hydrochloride of Example 3 (21.5 parts, 0.1 mole); 90 percent paraformaldehyde (3.7 parts, 0.11 mole); 70 percent aqueous orthophosphorous acid (12.9 parts, 0.11 mole); and water (6.0 parts) was heated at its reflux temperature for 3 hours. The product could not be isolated as a filterable solid due to its hygroscopic nature. The solution containing 61.9 percent of the title compound was used for testing without any further purification.

EXAMPLE 7

N,N'-Methylenebis(tetrahydro-3-thiophenamine)1,1,1',1'-tetraoxide

This intermediate compound was prepared by refluxing a solution of tetrahydro-3-thiophenamine 1,1-dioxide of Example 1 (13.5 parts, 0.1 mole); and 90 percent paraformaldehyde (1.7 parts, 0.05 mole) in methanol (50 ml.) for 5 hours. An off-white crystalline product was formed on cooling the mixture to room temperature. Yield 68 percent, m.p. 180°–184° C.

EXAMPLE 8

N,N'-Methylenebis-[tetrahydro-N-(phosphonomethyl)-3-thiophenamine]1,1,1',1'-tetraoxide A mixture of N,N'-methylenebis(tetrahydro-3-thiophenamine) 1,1,1',1'-tetraoxide of Example 7 (14.1 parts, 0.05 mole); 90 percent paraformaldehyde (3.7 parts, 0.11 mole); 70 percent aqueous orthophosphorous acid (12.9 parts, 0.11 mole); and concentrated hydrochloric acid (4.6 parts, 0.05 mole) was refluxed for 3 hours. The cooled solution was poured into and titurated under ethanol. A tan colored solid weighing 8.7 g. (36 percent yield) was obtained. The product was identified by its characteristic infrared peaks.

EXAMPLE 9

N,N'-Ethylenebis(tetrahydro-3-thiophenamine) 1,1,1',1'-tetraoxide

A mixture of 2,5-dihydrothiophene 1,1-dioxide (236.4 parts, 2.0 moles); ethylenediamine (480.8 parts, 8 moles); and water (600 ml.) was heated at 70°–80° C. for 4 hours. The water and unreacted ethylenediamine were distilled under reduced pressure. Benzene (750 ml.) was added to the residue and the residual water was removed by azeotropic distillation. After removing the benzene, a reddish colored viscous oil in the amount of 375 g. (63 percent yield) that solidified on cooling was obtained.

EXAMPLE 10

N,N'-Ethylenebis-[tetrahydro-N-(phosphonomethyl)-3-thiophenamine]1,1,1',1'-tetraoxide The procedure of Example 8 was repeated substituting N,N'-ethylenebis (tetrahydro-3-thiophenamine) 1,1,1',1'-tetraoxide (29.6 parts, 0.1 mole) for the methylenebis compound of Example 8. A yield of 26.2 g. (54.1 percent) of a hygroscopic, white solid was obtained.

EXAMPLE 11

3-Hydrazinotetrahydrothiophene 1,1-Dioxide Hydrochloride

A mixture of hydrazine hydrate (64 percent hydrazine, 250 ml.) and 2,5-dihydrothiophene 1,1-dioxide (150.0 parts, 1.27 moles) was heated at 60°–63° C. for 5 hours. The excess of hydrazine was removed under reduced pressure. The viscous, slightly discolored residue was dissolved in methanol (500 ml.) and acidified with concentrated hydrochloric acid. The hydrochloride was dried in vacuo over $P_2O_5$. m.p. 193°–194° C., wt. 219.9 g. (92.6 percent yield).

EXAMPLE 12

3-Hydrazinotetrahydro-N,N-bis(phosphonomethyl)thiophene 1,1-dioxide

A mixture of 3-hydrazinotetrahydrothiophene 1,1-dioxide hydrochloride (56.0 parts, 0.3 mole); 90 percent paraformaldehyde (22.1 parts, 0.66 mole); 70 percent aqueous orthphosphorous acid (77.3 parts, 0.66 mole); and water (236.6 parts) was heated at reflux temperature for 3 hours. The dark solution containing 25.86 percent of the title compound was tested without isolating the product.

EXAMPLE 13

3,4-Diaminotetrahydrothiophene 1,1-dioxide dihydrochloride

A suspension of 3,4-dibromotetrahydrothiophene 1,1-dioxide (139.0 parts) in 29 percent ammonium hydroxide (250 ml.) was heated in a 1 liter stainless steel autoclave at 80°–86° for 2 hours. The clear solution obtained was concentrated under reduced pressure to a yellow viscous liquid which was filtered, dissolved in ethanol (75 ml.) and acidified with concentrated hydrochloric acid to obtain the title compound as a white crystalline solid. The yield was poor, about 5 percent of the theory.

EXAMPLE 14

Tetrahydro-N,N,N',N'-tetrakis(phosphonomethyl)-3,4-thiophenediamine 1,1-dioxide A mixture of 3,4-diaminotetrahydrothiophene 1,1-dioxide dihydrochloride (2.0 parts, 0.0089 mole); 90 percent paraformaldehyde (1.31 parts, 0.039 mole); 70 percent aqueous orthophosphorous acid (4.2 parts, 0.035 mole); and water (2 parts) was heated at the reflux temperature for one and a half hours. The resulting viscous liquid was poured into ethanol and the precipitated solid was filtered. The title compound was identified by its characteristic infrared peaks and by molecular weight determination. Yield 33 percent.

The phenomenon known as the "threshold effect" has been used for years to control scale deposition. This "threshold effect" is the prevention of precipitation from supersaturated solutions of such scaling solids as calcium carbonate, calcium sulfate, and barium sulfate by very small quantities, usually a few parts per million, of the inhibitor. Polyphosphates exhibit this phenomenon but these compounds are not stable in aqueous solution and revert to orthophosphates. We have tested the aminoalkylenephosphonic acids of this invention for this "threshold effect" and the following examples demonstrate that these new compounds do prevent scaling by this "threshold effect".

EXAMPLE 15

Calcium carbonate antiprecipitation tests

To evaluate the effect of the aminoalkylenephosphonic acids of this invention on the precipitation of calcium carbonate, measured volumes of stock solution (prepared with demineralized water) of the phosphonic acids or their sodium salts were added to 100 ml. portions of a calcium chloride solution (0.2936 g. $CaCl_2.2H_2O$ per 100 ml. of solution). Then 100 ml. of a sodium bicarbonate solution (0.168 g. $NaHCO_3$ per 100 ml. of solution) was added to each portion of calcium chloride solution. The test solutions were then agitated on a gyratory shaker table for 18 hours at a temperature of 25° C. At the end of this time, insoluble material was removed by filtration through a Millipore membrane filter, and the calcium ion concentration in the filtrate was determined with an atomic absorption spectrophotometer. The percent inhibition was calculated and the results are included in Table 1. The compounds tested were as follows:

A. Tetrahydro-N,N-bis(phosphonomethyl)-3-thiophenamine 1,1-dioxide (30 percent)
B. Thirty percent solution of the trisodium salt of A
C. A solution containing 15 percent of the trisodium salt of A and 15 percent of a poly(acrylic acid) having a molecular weight of about 4000
D. Tetrahydro-N,N,N',N'-tetrakis(phosphonomethyl)-3,4-thiophenediamine 1,1-dioxide (30 percent)
E. 3-Hydrazinotetrahydro-N,N-bis(phosphonomethyl)-thiophene 1,1-dioxide (30 percent)
F. Tetrahydro-N-(2-hydroxyethyl)-N-(phosphonomethyl)-3-thiophenamine 1,1-dioxide (30 percent)

Table 1

Inhibition of calcium carbonate precipitation at pH 8.5 and pH 9.0

| Concentration parts per million | Test pH | A | B | C | D | E | F |
|---|---|---|---|---|---|---|---|
| | | | | percent inhibition | | | |
| 1 | 8.5 | 83 | 92 | 88 | 78 | 82 | 27 |
| 3 | | 84 | 87 | 92 | 73 | 82 | 25 |
| 5 | | 78 | 92 | 92 | 73 | 77 | 27 |
| 10 | | 85 | 91 | 93 | 71 | 79 | 25 |
| 25 | | 73 | 93 | 92 | 70 | 100 | 38 |
| 50 | | 71 | 94 | 91 | 70 | 91 | 32 |
| 1 | 9.0 | — | 9 | 18 | — | 78 | — |
| 3 | | — | 11 | 21 | — | 79 | — |
| 5 | | — | 89 | 23 | — | 79 | — |
| 10 | | — | 85 | 80 | — | 79 | — |
| 25 | | — | 16 | 94 | — | 70 | — |
| 50 | | — | 86 | 77 | — | 86 | — |

EXAMPLE 16

Calcium sulfate antiprecipitation tests

Inhibition of calcium sulfate precipitation by the aminoalkylenephosphonic acids of this invention was evaluated by adding the desired volumes of stock solutions of the phosphonic acids or their sodium salts (prepared with demineralized water) to 10-ml. aliquots of a calcium chloride solution containing 162.9 g. of of $CaCl_2$ per liter. The volume of each was made up to 175 ml. with demineralized water, and the pH was adjusted to 7.0 with dilute NaOH or HCl. A 25-ml. aliquot of a sodium sulfate solution (83.84 g. $Na_2SO_4$ per liter) was then added to each. The test solutions were maintained for 18 hours at a temperature of 50° C. A portion of each was filtered while still hot to remove insoluble materials and the filtrate was analyzed for calcium by means of an atomic absorption instrument. The percent inhibition was calculated and the results are included in Table 2. Compounds B, E, and F included in this test were the same as described in Example 15. Compound G was a solution containing 20 percent of the trisodium salt of tetrahydro-N,N-bis(phosphonomethyl)-3-thiophenamine 1,1-dioxide and 10 percent of a poly (acrylic acid) having the molecular weight of about 4000. Compound H was a solution containing 15 percent of tetrahydro-N,N-bis(phosphonomethyl)-3-thiophenamine 1,1-dioxide and 15 percent of a poly(acrylic acid) having a molecular weight of about 4000.

Table 2

Inhibition of calcium sulfate precipitation at pH 7

| Concentration parts per million | B | G | H | E | F |
|---|---|---|---|---|---|
| | | Percent inhibition | | | |
| 1 | 40 | 50 | 38 | 38 | 41 |
| 3 | 52 | 59 | 41 | 38 | 38 |
| 5 | 55 | 83 | 43 | 38 | 39 |
| 10 | 78 | 91 | 56 | 38 | 43 |
| 25 | 95 | 91 | 91 | 40 | 61 |
| 50 | 100 | 92 | 100 | 45 | 88 |

EXAMPLE 17

Barium sulfate antiprecipitation tests

To evaluate the effect of the aminoalkylenephosphonic acids of this invention in inhibiting the precipitation of barium sulfate, the desired volumes of stock solutions of the phosphonic acids or their sodium salts (prepared with demineralized water) were added to 10-ml. aliquots of a barium chloride solution containing 5.35 g. $BaCL_2.H_2O$ per liter. The volume of each was made up to 175 ml. with demineralized water, and the pH was adjusted to 7.0 with dilute NaOH or HCl. A 25-ml. aliquot of a sodium sulfate solution (1.24 g. $Na_2SO_4$ per liter) was then added to each. The test solutions were agitated on a gyratory shaker table for 18 hours at 25° C. At the end of this time, insoluble material was removed by filtration and the barium ion concentration was determined with an atomic absorption unit. The percent inhibition was calculated and the results are included in Table 3. Compound C was described in Example 15 and Compound H was described in Example 16. Compound I was an aqueous solution containing 22.5 percent of the trisodium salt of tetrahydro-N,N-bis(phosphonomethyl)-3-thiophenamine 1,1-dioxide and 7.5 percent of a poly(acrylic acid) having a molecular weight of about 4000. Compound J was an aqueous solution containing 7.5 percent of tetrahydro-N,N-bis(phosphonomethyl)-3-thiophenamine 1,1-dioxide and 22.5 percent of a poly(acrylic acid) having a molecular weight of about 4000. Since the percent inhibition results were lower than those obtained in Examples 15 and 16, a well known scale inhibitor was included in this test for comparison. Thus, Compound K is a 50 percent aqueous solution of nitrilotris(methylenephosphonic acid) and the effectiveness of this compound was less than that of the combinations containing tetrahydro-N,N-bis(phosphonomethyl)-3-thiophenamine 1,1-dioxide.

Table 3

Inhibition of barium sulfate precipitation at pH 7

| Concentration parts per million | I | C | J | H | K |
|---|---|---|---|---|---|
| | | Percent inhibition | | | |
| 5 | 1 | 1 | 1 | 10 | 5 |
| 10 | 2 | 1 | 1 | 16 | 5 |
| 25 | 11 | 15 | 12 | 21 | 6 |
| 50 | 20 | 11 | 14 | 18 | 12 |

EXAMPLE 18

Corrosion inhibiting properties of Tetrahydro-N,N-bis(phosphonomethyl)-3-thiophenamine 1,1-dioxide in combination with poly(acrylic acid) and Water Soluble Zinc Compounds.

This example illustrates the corrosion-inhibiting properties of compositions containing tetrahydro-N,N- bis(phosphonemethyl)-3-thiophenamine 1,1-dioxide, poly(acrylic acid), (molecular weight-4000), and water soluble zinc compounds.

The test apparatus included a sump, a flow circuit, a circulating pump, and a heater. The test fluid was tap water from the City of Memphis water system. The water did not come in contact with any metal except for test coupons placed within the circuit in a manner simulating flow, impingement, and sump conditions. In addition to the normal sump coupon, an additional steel coupon was coupled with a copper coupon and placed in the sump. The test coupons were 1010 mild steel, and the circulating water had a calcium hardness as CaCO3 of 25 parts per million, a magnesium hardness as CaCO3 of 18 parts per million, chloride as Cl of 10 parts per million, and sulfate as SO4 of 2.5 parts per million.

The temperature during the test was maintained about 50° C. and the pH was adjusted to 6.5 at the beginning of the test. The water was circulated continuously through the system containing the coupons for a period of 72 hours. The steel coupons were then removed and examined for scale. No scale was observed on any of the coupons protected by the compositions of this invention. The coupons were then cleaned, weighed, and the corrosion rates calculated as milligrams of weight loss per square decimeter per day. The corrosion rates are included in Table 4.

Table 4

Corrosion inhibition with products containing tetrahydro-N N-bis(phosphonomethyl)-3-thiophenamine 1,1-dioxide

| Corrosion Inhibitor | | | Corrosion rate in milligrams per decimeter$^2$ per day | | | |
|---|---|---|---|---|---|---|
| Phosphonic Acid | Poly (acrylic acid) Parts per million | Zinc | Flow | Impingement | Sump | Copper Couple |
| none | none | none | 384 | 221 | 300 | 300 |
| 10 | none | 2 | 32 | 34 | 19 | 30 |
| 20 | none | 4 | 6 | 6 | 3 | 8 |
| 10 | 10 | 2 | 15 | 25 | 7 | 41 |
| 20 | 20 | 4 | 4 | 6 | 2 | 4 |
| 20 | 20 | none | 8 | 9 | 5 | 14 |

The invention having thus been described, what is claimed and desired to be secured by Letters Patent is:

1. As a new composition of matter an aminoalkylenephosphonic acid or an alkali metal salt thereof having the formula:

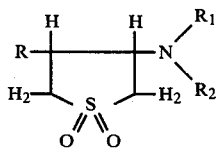

wherein R is hydrogen or

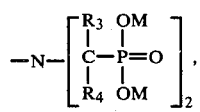

R1 is hydrogen or

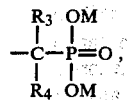

R2 is an alkyl group containing 1 to 4 carbon atoms, 2-hydroxyethyl, 2-hydroxypropyl, 3-chloro-2-hydroxypropyl,

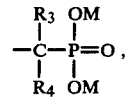

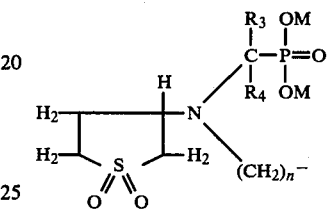

or 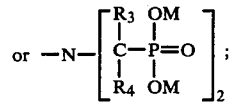

R3 and R4 may be the same or different and are selected from the group consisting of hydrogen and an alkyl group containing 1 to 4 carbon atoms; n is 1 or 2; M is hydrogen or an alkali metal; with the proviso that when R is

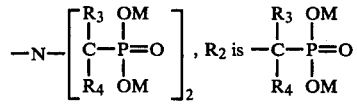

and with the further proviso that R1 is hydrogen only when R2 is

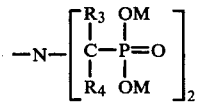

2. The compound according to claim 1 identified as tetrahydro-N,N-bis(phosphonomethyl)-3-thiophenamine 1,1-dioxide.

3. The compound according to claim 1 identified as tetrahydro-N-methyl-N-(phosphonomethyl)-3-thiophenamine 1,1-dioxide.

4. The compound according to claim 1 identified as N-ethyltetrahydro-N-(phosphonomethyl)-3-thiophenamine 1,1-dioxide.

5. The compound according to claim 1 identified as tetrahydro-N-(phosphonomethyl)-N-propyl-3-thiophenamine 1,1-dioxide.

6. The compound according to claim 1 identified as tetrahydro-N-isopropyl-N-(phosphonomethyl)-3-thiophenamine 1,1-dioxide.

7. The compound according to claim 1 identified as N-n-butyltetrahydro-N-(phosphonomethyl)-3-thiophenamine 1,1-dioxide.

8. The compound according to claim 1 identified as N-sec-butyltetrahydro-N-(phosphonomethyl)-3-thiophenamine 1,1-dioxide.

9. The compound according to claim 1 identified as N-isobutyltetrahydro-N-(phosphonomethyl)-3-thiophenamine 1,1-dioxide.

10. The compound according to claim 1 identified as N-tert-butyltetrahydro-N-(phosphonomethyl)-3-thiophenamine 1,1-dioxide.

11. The compound according to claim 1 identified as tetrahydro-N-(2-hydroxyethyl)-N-(phosphonomethyl)-3-thiophenamine 1,1-dioxide.

12. The compound according to claim 1 identified as tetrahydro-N-(2-hydroxypropyl)-N-(phosphonomethyl)-3-thiophenamine 1,1-dioxide.

13. The compound according to claim 1 identified as N-(3-chloro-2-hydroxypropyl) tetrahydro-N-(phosphonomethyl)-3-thiophenamine 1,1-dioxide.

14. The compound according to claim 1 identified as N,N'-methylenebis-[tetrahydro-N-(phosphonomethyl)-3-thiophenamine]1,1,1',1'-tetraoxide.

15. The compound according to claim 1 identified as N,N'-ethylenebis-[tetrahydro-N-(phosphonomethyl)-3-thiophenamine]1,1,1',1'-tetraoxide.

16. The compound according to claim 1 identified as 3-hydroazinotetrahydro-N,N-bis(phosphonomethyl)-thiophene 1,1-dioxide.

17. The compound according to claim 1 identified as tetrahydro-N,N, N',N'-tetrakis(phosphonomethyl)-3,4-thiophenediamine 1,1-dioxide.

* * * * *